United States Patent [19]

O'Leary

[11] Patent Number: 4,946,792
[45] Date of Patent: Aug. 7, 1990

[54] PROCESS FOR DEBRIDING BONE

[75] Inventor: Robert K. O'Leary, Spring Lake, N.J.

[73] Assignee: Osteotech, Inc., Shrewsbury, N.J.

[21] Appl. No.: 395,782

[22] Filed: Aug. 18, 1989

[51] Int. Cl.$^5$ ............................................. C07G 15/00
[52] U.S. Cl. .................................... 435/268; 424/549; 435/1; 435/267; 435/264; 623/16
[58] Field of Search ........................... 435/267, 268, 1; 424/95; 623/16

[56] References Cited

U.S. PATENT DOCUMENTS 4,399,123  8/1983  Oliver et al. .
4,642,292  2/1987  Reid et al. .
4,656,137  4/1987  Balassa .
4,801,451  1/1989  Hellgreen et al. .

OTHER PUBLICATIONS

Tobiume-Chem. Abst., vol. 90 (1979), p. 12274p.

Primary Examiner—Sam Rosen
Attorney, Agent, or Firm—Dilworth & Barrese

[57] ABSTRACT

Bone is enzymatically debrided prior to undergoing further processing which renders the bone suitable for osteoprosthetic use.

20 Claims, No Drawings

PROCESS FOR DEBRIDING BONE

BACKGROUND OF THE INVENTION

This invention relates to a process for debriding bone and is principally concerned with the removal of the periosteum, a specialized connective tissue covering all bones of the body, as a preliminary step in the processing of bone which is intended for osteoprosthetic use.

Bone and related tissue referred to as allografts, hereinafter collectively referred to as "bone" for the sake of convenience, are used in numerous surgical specialities to repair or replace defective or damaged bones. The range of allograft transplants includes entire joints, sections of long bone, bone chips for surgical procedures such as spinal fusion and craniotomies and bone dust used in dental repair/reconstruction.

Prior to use in osteoprosthetic surgery, harvested bone tissue may be processed by any of a variety of procedures, e.g., defatting, demineralization, reshaping, and the like, which prepare the bone for grafting or implantation. As a necessary preliminary to these and other bone tissue processing techniques, connective tissue which tenaciously adheres to the bone, the periosteum, must be removed, a procedure referred to herein as "debridement". Up until now, it has been the practice to accomplish debridement of bone by purely mechanical techniques, a time-consuming, labor-intensive procedure which adds significantly to the cost of bone tissue intended for osteoprosthetic use.

SUMMARY OF THE INVENTION

It is a principal object of the invention to provide a process for the debridement of bone employing a proteolytic enzyme which loosens the periosteum facilitating its removal from the bone.

It is another object of the invention to provide such an enzymatic debridement process employing a permeation enhancer to provide more effective penetration of proteolytic enzyme and, optionally, one or more other substances such as disinfectants and antibiotics, into the periosteum.

It is yet another specific object of the invention to remove enzymatically loosened periosteum from bone employing a high velocity fluid stream, e.g., of water.

In keeping with these and other objects of the invention, there is provided a process for the debridement of harvested bone having its periosteum intact which comprises contacting the bone with a proteolytic enzyme solution under proteolytic conditions for a period of time sufficient to loosen the periosteum from the underlying bone surface and thereafter removing the loosened periosteum from the bone.

In addition to significantly reducing the time required to effect debridement compared with that required for the older mechanical methods, the enzymatic debridement process of this invention greatly facilitates the removal of periosteum from areas which are difficult to reach with mechanical debridement devices such as scalpels and curettes. Thus, in addition to providing a relatively rapid process of bone debridement, the process of the present invention greatly facilitates the removal of periosteum and related connective tissue such as cartilage, tendons and ligaments from areas of bone which undergo mechanical debridement only with particular difficulty.

DESCRIPTION OF THE PREFERRED EMBODIMENTS

Any proteolytic enzyme or combination of proteolytic enzymes which effect the loosening of the periosteum can be used herein Suitable proteolytic enzymes include ficin, pepsin, trypsin, chymotrypsin, papain, and the like, with trypsin being preferred.

The enzyme(s) must, of course, be employed under conditions which promote proteolytic activity. For example, in the case of papain, the temperature can be anywhere in the range of from about ambient to about 70° C., preferably from about 25° to about 55° C., and the pH can be within the range of from about 3 to 9, preferably from about 4 to about 7. In the case of trypsin, similar temperature ranges are appropriate and the pH is preferably set at about 8 to 9 for optimum activity.

The enzyme or enzyme mixture is dissolved in water and/or other suitable carrier, preferably one which is sterile such as sterile physiological saline, to provide a total protease activity of, e.g., from about 0.001 to about 0.1, and preferably from about 0.001 to about 0.01, enzyme units per mg (expressed as micromole tyrosine equivalents per minute with casein as substrate). The enzyme solution can contain a variety of additives including organic and inorganic salts, gel-forming materials, antimicrobials, surface active agents, and the like.

In general, contact times of the bone with the enzyme solution of from 30 minutes to several hours or even days will effect a degree of loosening of the periosteum which greatly facilitates its removal from the underlying bone.

It can also be advantageous to accomplish debridement employing a stream of high velocity fluid to remove the enzymatically loosened periosteum from the surface of the bone. A high velocity stream of sterile water or physiological saline is preferably utilized for this purpose and its application follows the soaking of the bone in the enzyme solution for the contact times mentioned above.

If desired, the debridement process herein can be accompanied by exposure of the bone to sterilizing ultraviolet radiation (e.g., of 254 millimicrons wavelength). Such exposure can be achieved in a variety of ways, e.g., by placing the bone in an environment suffused with ultraviolet radiation or by localized application of ultraviolet radiation upon the surface of the enzymatically loosened periosteum while the periosteum is undergoing removal from the bone. When, e.g., a high velocity stream of water is used to effect such removal, one or more optical fibers coincident with the longitudinal axis of the stream and preferably positioned within the central portion thereof delivers ultraviolet radiation to the surface of the periosteum simultaneously with the impingement of the stream thereon.

In accordance with a particular embodiment of the enzymatic bone debridement process herein, an enzyme penetration or permeation enhancer is included in the enzyme debridement solution to enhance penetration or diffusion of the enzyme into the periosteum or to otherwise accelerate the loosening of the periosteum from the underlying bone. Suitable penetration or permeation enhancers include surface active agents which may be of the cationic, non-inonic, anionic or amphoteric variety; glycerol monolaurate; hexamethylene lauramide; dimethyl formamide; propylene glycol; diethyltoluamide; N-methyl-1-2-pyrrolidone; declymethylsulfoxide; benzyl alcohol; dimethyl sulfoxide; alkyl-N-N-dialkylsubstituted amino acetates; lecithin; dimethylacetamide; laurocapram; dodecyl-L-pyroglutamate; 1-oxohydrocarbyl-substituted azacyclohexanes; azone; hydroxyethyl acetamide; tetrahydrofurfuryl alcohol; methyl laurate; isopropyl palmitate; isopropyl myristate; isopropyl stearate; and, enamines. Preferred permeation enhancers are isopropyl palmitate and isopropyl myristate. The amount of permeation enhancer employed can vary widely with quantities of from about 0.01 to about 10 weight percent of enzyme debridement solution being effective in most cases.

The enzyme debridement solution can also contain one or more other components which are generally beneficial to the process, e.g., antibiotics and/or disinfectant agent(s). Antibiotics which can be employed include bacitracin, polymyxin B sulfate, erythromycin, neomycin, penicillin, tetracyclines, viomycin, chloromycetin, streptomycins, cefazolin, ampicillin, tobramycin, clindamycin, and gentamicin. Disinfectant(s) which can be employed in accordance with the present invention are generally present in an aqueous solution and are administered in an effective disinfecting amount. Examples of disinfectants which can be employed include ethylene oxide, propylene oxide, ethanol, hydrogen peroxide (preferably as 10% hydrogen peroxide in aqueous solution), chlorine dioxide, chlorahexidene gluconate, glutaraldehyde, formaldehyde, peracetic acid (hydrogen peroxide and acetic acid in aqueous solution), povadone iodide (polyvinylpyrrollidone), sodium hypochlorite, quaternary ammonium compounds, cetyl alcohol and benzalkonium chloride. A preferred disinfectant is an aqueous ethanol solution. Optimum amounts of these and other optional components of the enzyme debridement solution can be readily determined employing routine experimentation.

The following example is illustrative of the bone debridement process of the present invention.

EXAMPLE

A section of femoral bone which has been harvested under aseptic conditions in accordance with accepted practice and from which the soft tissue has previously been removed is placed in a physiological saline solution of commercial trypsin (TRYPURE, Novo Industri, Copenhagen, Denmark) assaying approximately 0.001 enzyme units per mg. The temperature is maintained at about 25° C. and the pH at a level of about 8. After a period of 4 hours, the periosteum is found to be loosened from the bone and is easily removed therefrom.

What is claimed is:

1. A process for the debridement of harvested bone having its periosteum intact which comprises contacting the periosteum with a proteolytic enzyme solution under proteolytic conditions for a period of time sufficient to loosen the periosteum from the underlying bone surface and thereafter removing the enzymatically loosened periosteum from the bone.

2. The process of claim 1 wherein the proteolytic enzyme is selected from the group consisting of ficin, pepsin, trypsin, chymotrypsin and papain.

3. The process of claim 1 wherein the temperature of contacting ranges from about 20° C. to about 70° C.

4. The process of claim 1 wherein the temperature of contacting ranges from about 25° to about 55° C.

5. The process of claim 1 wherein the enzyme is papain and the pH ranges from about 3 to 9.

6. The process of claim 1 wherein the enzyme is trypsin and the pH ranges from about 8 to 9.

7. The process of claim 1 wherein the enzyme solution exhibits an activity of from about 0.0001 to about 0.1 enzyme units per mg.

8. The process of claim 1 wherein the enzyme solution exhibits an activity of from about 0.001 to about 0.01 enzyme units per mg.

9. The process of claim 1 wherein the contact time of the bone with the enzyme solution is at least about 30 minutes.

10. The process of claim 1 wherein the enzyme solution is a sterile physiological saline solution.

11. The process of claim 1 wherein the enzyme solution contains a permeation enhancer.

12. The process of claim 11 wherein the permeation enhancer is a surface active agent.

13. The process of claim 1 wherein the enzyme solution contains at least one member of the group consisting of antibiotic and disinfectant.

14. The process of claim 13 wherein the disinfectant is ethanol.

15. The process of claim 1 wherein the enzyme solution contains a permeation enhancer and at least one member of the group consisting of antibiotic and disinfectant.

16. The process of claim 1 wherein the enzyme solution contains an enzyme permeation enhancing amount of at least one enzyme permeation enhancing surface active agent and a disinfecting amount of ethanol.

17. The process of claim 1 wherein the enzymatically loosened periosteum is removed from the bone by the impact of a high velocity fluid stream directed against the periosteum.

18. The process of claim 17 wherein the high velocity fluid stream is water or physiological saline.

19. The process of claim 1 wherein removal of the enzymatically loosened periosteum from the bone is accompanied by exposure of the bone to sterilizing ultraviolet radiation.

20. The process of claim 18 wherein removal of the enzymatically loosened periosteum from the bone is accompanied by exposure of the bone to sterilizing ultraviolet radiation directed against the surface of the periosteum upon which the high velocity fluid stream impinges.

* * * * *